(12) United States Patent
Silverstone

(10) Patent No.: US 7,272,440 B2
(45) Date of Patent: Sep. 18, 2007

(54) METHOD AND APPARATUS FOR TREATMENT OF VIRAL DISEASES

(76) Inventor: Leon M. Silverstone, 3248 Brant St., San Diego, CA (US) 92103

( * ) Notice: Subject to any disclaimer, the term of this patent is extended or adjusted under 35 U.S.C. 154(b) by 128 days.

(21) Appl. No.: 10/624,816

(22) Filed: Jul. 22, 2003

(65) Prior Publication Data

US 2004/0181264 A1   Sep. 16, 2004

Related U.S. Application Data

(63) Continuation of application No. 09/727,287, filed on Nov. 29, 2000, now Pat. No. 6,618,625.

(51) Int. Cl.
*A61N 1/00* (2006.01)
(52) U.S. Cl. .......................................................... 607/2
(58) Field of Classification Search .................. 607/50, 607/72, 76, 46, 74, 73, 115, 15, 2; 600/382, 600/372
See application file for complete search history.

(56) References Cited

U.S. PATENT DOCUMENTS

| | | | |
|---|---|---|---|
| 4,786,277 A | 11/1988 | Powers et al. ................. 604/20 |
| 4,913,148 A * | 4/1990 | Diethelm ...................... 607/72 |
| 5,133,352 A * | 7/1992 | Lathrop et al. ................ 607/75 |
| 5,169,384 A * | 12/1992 | Bosniak et al. ................ 604/20 |
| 5,470,349 A | 11/1995 | Kleditsch et al. .............. 607/75 |
| 5,607,461 A | 3/1997 | Lathrop |
| 5,817,142 A | 10/1998 | Corder |
| 5,891,182 A | 4/1999 | Fleming |
| 5,925,071 A | 7/1999 | Story |
| 6,041,262 A * | 3/2000 | Beder .......................... 607/139 |
| 6,083,250 A | 7/2000 | Lathrop ........................ 607/50 |
| 6,104,952 A | 8/2000 | Tu et al. ........................ 604/20 |
| 6,389,319 B1 | 5/2002 | Lee .............................. 607/76 |
| 6,554,781 B1 * | 4/2003 | Carter et al. ................. 600/594 |
| 6,597,949 B1 * | 7/2003 | Dhurjaty ........................ 607/5 |

FOREIGN PATENT DOCUMENTS

| | | |
|---|---|---|
| WO | WO98/52642 | 11/1998 |
| WO | WO99/38566 | 8/1999 |

* cited by examiner

*Primary Examiner*—Scott M. Getzow
(74) *Attorney, Agent, or Firm*—Knobbe Martens Olson & Bear LLP

(57) ABSTRACT

An apparatus and method for treating viral infections delivers electrical stimulation to the skin or mucosa of a patient. The electrical stimulation is applied as a series of electrical pulses having different electrical characteristics. The apparatus may include a housing having at least two electrodes supplied with both AC and DC voltage, and powered by a battery. The electrodes are designed so as to maximize contact with the patient.

17 Claims, 4 Drawing Sheets

METHOD AND APPARATUS FOR TREATMENT OF VIRAL DISEASES

RELATED APPLICATIONS

This is a continuation application of copending application Ser.No. 09/727,287 entitled METHOD AND APPARATUS FOR TREATMENT OF VIRAL DISEASES filed on Nov. 29, 2000, now U.S. Pat. No. 6,618,625 issued on Sep. 9, 2003 which application is hereby incorporated by reference in its entirety.

BACKGROUND OF THE INVENTION

1. Field of the Invention

The invention relates to a method and apparatus for delivering electrical stimulation to pathological tissue, and more particularly, to treating viral infections by applying a series of electrical pulses having different maximum amplitudes to the affected skin or mucosa.

2. Description of the Related Art

Viruses are the smallest infectious agents and contain a molecule of nucleic acid (RNA or DNA) as their genome. Nucleic acid is enclosed in a protein shell. The viral nucleic acid contains information necessary for programming the infected host cell to synthesize the specific number of macromolecules. Toward the end of the replicative cycle, more viral nucleic acids and coat proteins are produced. The coat proteins assemble together to form the symmetrical protein shell which encloses the nucleic acid genome.

There are eight identified herpes viruses that have been associated with human disease conditions. The alpha-herpes viruses, HSV-1, HSV-2, and VZV-2, known as oral herpes, genital herpes, and herpes zoster respectively, are neurotropic since they actively infect nervous tissue. Five other herpes viruses are lymphotropic since they replicate in the lymphatic system. These include HCMV (human cytomegalovirus), HHV-6, HHV-7, HHV-8 (KHSV) and EBV. HHV-6 has been associated with multiple sclerosis. HHV-8 (KHSV) and EBV have been linked to the human cancers Kaposi's sarcoma and Epstein-Barr disease.

Disease states are also caused by a variety of other viruses. Viral hepatitis is a serious liver disease of particular concern for healthcare professionals. One form of hepatitis, hepatitis C, is considered responsible for approximately 10,000 deaths per year. The human papilloma virus (HPV) is responsible for most of the cervical cancers worldwide, genital warts and the formation of verrucae, warts that form on the soles of the feet. HPV has also been associated with several oral cancers. In addition, the HIV virus has killed more than 19 million people and infected 34 million more, causing an epidemic that will continue to devastate communities around the world.

Oral Herpes: The HSV-1 Virus

Herpes simplex virus (HSV) infections of the oral tissues are among the most common infectious illnesses involving man. Both primary (initial) and recurrent forms of the infection occur, these being referred to as acute primary herpetic gingivo stomatitis, and recurrent herpes labialis. Although oral herpes infections may be considered primarily nuisance diseases, gingivostomatitis can be a very painful and debilitating illness, while recurrent oral herpes in immunosuppressed subjects may be severe and even life-threatening (Overall, 1979; Ho, 1979; Faden et al, 1977).

The vast majority of oral herpes infections are caused by the HSV type 1 strain. There are no precise data for the frequency of oral herpes infections. It is estimated that there are about 500,000 cases of herpes stomatitis each year in the U.S. Recurrent herpes labialis occurs in approximately one-third of the population and the mean number of episodes per year in individuals with recurrent disease is 1.6 (Overall, 1979). This projects at about 100 million episodes of herpes labialis in the U.S. each year.

There are several factors that contribute to the significance of oral herpes infections. First, herpes gingivostomatitis can be a severe illness. Fever, toxicity, and exquisitely painful mouth lesions may interfere with fluid intake and require hospitalization for intravenous fluids. Second, frequent recurrent lesions of the lips are of cosmetic concern, particularly in females. Third, cold sores may be the source of HSV for transmission to immunosuppressed or other hospitalized patients. Fourth, oral herpes in the immunosuppressed patient is often a severe, life-threatening disease. Finally, there is currently no satisfactory and effective form of therapy for either primary or recurrent mucocutaneous HSV disease in the normal host.

Most patients develop vesicles within 12 hours, which rupture to form ulcers or crusts in 36 to 48 hours. Most patients lose the crust and have healed ulcers by day 8 to 10. Results from clinical trials on recurrent herpes labialis has shown that about 25% of patients had episodes one or more times a month, almost two-thirds had one episode every 2-4 months, and less than 25% had an episode less often than every 4 months (Spraunce et al, 1977).

Genital Herpes: The HSV-2 Virus

Despite the emphasis and publicity on safe sex to prevent AIDS, a recent study by the Centers for Disease Control has shown that genital herpes has increased fivefold among white teenagers since the late 1970's, and doubled among whites in their 20's (*New Eng. J of Medicine*,Oct. 16, 1997). One in five Americans over the age of 12 years carries the virus that causes genital herpes, with 500,000 new cases occurring each year.

It is currently standard practice in the U.S. to perform Cesarean delivery on pregnant women with recurrent herpes to reduce the risk of transmission of the virus to newborns (*J. Obstetrics & Gynecology*, October, 1996). In spite of this, 20-30% of all infants born via Cesarean delivery still have the herpes virus. More than 40% of newborns infected with HSV die or suffer neurologic impairment. What exacerbates this problem is that women are 45% more likely to be infected with HSV-2 than men. Since there has been a dramatic increase in genital herpes among the younger generations, it means that a substantial number of women entering their childbearing years are infected with HSV-2, or are at risk of contracting infection. Despite antiviral therapy, neonatal herpes is still a major life threatening infection.

After inoculation and limited replication at genital sites, HSV-2 ascends along neuronal axons to establish latent infection in the lumbosacral ganglia. During this initial phase, infectious virus is present at genital sites for days or weeks, usually without lesions. When a new cycle of viral replication is triggered, reactivation occurs and infectious virus is delivered back down the neural pathways to the mucosa or skin. The return of infectious virus to genital sites during HSV-2 reactivation rarely causes any symptoms. HSV-2 is a chronic, persistent infection that causes subclinical reaction in about 1% of infected persons. Since about 45-50 million people in the U.S. are infected, HSV-2 can spread efficiently and silently through the population. People who have sexual contact with many partners will frequently have exposure to an infected person who is shedding HSV-2. As the overall prevalence of HSV-2 infection continues to rise, contact with fewer partners will permit exposure.

The concept that HSV persists in the nuclei of cells in the sensory ganglia suggests that any topical treatment will be ineffective in destroying the virus in these hidden locations. About 25 viruses have been placed in the HSV group and they all contain a core of double stranded DNA surrounded by a protein coat that exhibits isocahedril symmetry. This in turn is enclosed in an envelope which contains essential lipids. The structural proteins of herpes simplex virus include nine polypeptides which have been found in the enveloped virion, two polypeptides which are associated with the envelope, two arginine polypeptides within the virus core, as well as guanine and cytosine. The virus enters the cell either by fusion with the cell membrane or by pinocytosis. It is then uncoated and the DNA becomes associated with the nucleus. Soon after infection the virus codes for its own DNA polymerase and other enzymes such as thymidine kinase which is associated with the DNA replication.

A variety of treatments have been used for genital herpes but none is entirely satisfactory. No satisfactory vaccine has been found. In superficial infections, topical agents such as Idoxuridine, Triflurothymidine, or Acyclovir are sometimes effective. The drug of choice for the treatment of herpes simplex is Acyclovir which is the only FDA approved drug. Sales of Zovirax® (Burroughs Wellcome) were given at about $500M. Annual estimated sales for this product exceeded $2 billion worldwide in 1997. Administered orally for systemic absorption, Acyclovir is limited by several factors:
1) side effects include rash, nausea, vomiting, diarrhea, or pain, burning or itching at the site where the drug is applied, anorexia and possible eye injures.
2) cost; the average annual cost to a patient is around $1000.
3) emergence of drug-resistant virus strains.
4) presence of a large number of "early reactivation" patients for whom Acyclovir does not work.
5) a 6-10 day treatment cycle; patients with HSV-1 (oral herpes/cold sores) must decide if treatment is worth 6-10 days use of an expensive systemic drug with potential side effects.

First episodes of the virus should all be treated as early as possible with one of three available oral antiviral agents. Effective treatments include: Acyclovir (Zovirax™) where the usual dose is 200 mg five times daily. Valacyclovir HCl (Valtrex™) is an improved oral formulation of Acyclovir which requires less frequent dosing at 500 mg twice daily. Famciclovir (Famvir™) is the oral formulation of penciclovir and it is dosed for primary infections at 250 mg three times daily. Studies have proven all three drugs to be equally effective. In North America, first episode treatment is generally prescribed for 10 days, but in Europe and the UK, treatment is generally prescribed for 5 days. These antiviral medications can be taken orally very early in a recurrent episode.

Herpes Zoster

Herpes zoster, also known as shingles, is due to invasion of posterior root ganglia by the causative virus and is characterized by severe pain followed by a rash over cutaneous distribution of the affected nerve. The virus, varicella-zoster (VZ), causes two diseases, varicella (chickenpox) resulting from the first exposure to the virus in childhood, and zoster, a secondary infection due to reactivation of the latent VZ virus. Shingles is a painful and potentially debilitating disease that affects 750,000 people each year in the U.S. The condition is most commonly experienced by older Americans and is caused by a reactivation of the varicella-zoster virus, the same herpes virus which causes chickenpox. A major challenge for physicians in managing patients with shingles is alleviating the severe pain associated with an active shingles rash, as well as postherpetic neuralgia (long-term debilitating pain) which may occur following rash healing.

Herpes and Multiple Sclerosis

A strain of reactivated herpes virus may be associated with multiple sclerosis (MS), an autoimmune disorder in which the body attacks its own tissues. Results of a study conducted by scientists at the National Institute of Neurological Disorders and Stroke (NINDS) in Bethesda, Md., add to mounting evidence of the role of viral triggers in MS and may serve as the cornerstone for clinical trials using antiherpetic agents as a treatment. This is the first published large-scale study suggesting an association of a human herpes virus in the disease process of MS. In the study, more than 70 percent of patients with the relapsing-remitting form of MS showed an increased immune response to human herpes virus-6 (HHV-6) and approximately 35 percent of all MS patients studied had detectable levels of active HHV-6 in their serum. Scientists believe that there may be a point in time during the progression of MS when the virus, which lies dormant in the body for years, reactivates, accounting for its presence in a subset of MS patients. The study appears in the December 1997 issue of Nature Medicine.

As many as 350,000 Americans are affected by MS, which is most often diagnosed in patients between the ages of 20 and 40 and is characterized by muscle weakness, visual disturbances, and a variety of other neurological impairments. The array and severity of symptoms varies widely from patient to patient and women are more likely to be affected than men. The most common form of MS is the relapsing-remitting type. In this type of MS, new symptoms appear or existing ones become more severe, followed by periods of partial or total recovery. These flare-ups of new or intensified symptoms last for variable amounts of time. A second form of MS is a chronic and progressive one in which symptoms steadily worsen. HHV-6 is relatively new to scientists and is known to cause a common childhood illness, roseola. HHV-6 is known to be present in 90 percent of the adult American population as a result of infection during the first few years of life. Scientists believe that the reactivation of HHV-6 virus may be associated with the breakdown of the protective covering of nerves, called myelin. Reactivation is characteristic of herpes viruses. In the study, investigators screened the serum of 102 individuals, 36 of whom had MS. Of the 22 individuals with the relapsing-remitting form of MS, 73 percent had an increase in immune response to an early antigen of HHV-6, compared to only 18 percent of those participants who served as normal volunteers. In addition, the scientists detected HHV-6 DNA in the serum (a marker of active virus infection) of 15 of 50 individuals with MS. All 47 individuals without MS tested negative for the presence of active HHV-6 viral infection.

Human Papillomavirus

Human papillomavirus (HPV) is one of the most common sexually transmitted diseases. Genital HPV infections are widespread among sexually active adults. It is estimated that as many as 40 million Americans are infected with HPV, and the incidence of the disease appears to be increasing. More than 1000 types of HPV have been identified. Some cause common skin warts. Others are spread through sexual contact and result in genital warts.

HPV often results in an infection without any visible symptoms. Thus, individuals may not be aware of the infection or of the potential risk of transmission to others. Genital warts are spread by sexual contact and are highly contagious. Approximately two-thirds of people who have sexual contact with a partner with genital warts will develop warts, usually within about three months of contact.

In women, the warts occur on the outside and inside of the vagina, on the cervix, and around the anus. In men, the warts occur on the penis, scrotum, and around the anus. Genital warts often occur in clusters, and can be very tiny or can occur in large masses. Treatment includes the application of trichloracetic acid or podophyllin solution. Warts can be removed by cryosurgery, electrocautery or surgery. Although elimination of the warts is possible, the viral infection persists and warts often reappear after treatment.

To date, there are very few satisfactory treatments, vaccines, or cures for viral infection. Drug treatments, either topical or ingested, have shown generally limited benefits. As an alternative to the pharmaceutical approach, the electrical stimulation of infected tissues has been explored. These methods involve the application of electrodes to the skin near the infected region. Some examples are provided by U.S. Pat. No. 4,913,148 to Diethelm, U.S. Pat. No. 5,133,352 to Lathrop, et al., and U.S. Pat. No. 5,607,461 to Lathrop. The disclosures of each of these patents is hereby incorporated by reference in their entireties. Although this technique shows promise, to date, the devices and stimulation protocols used have been less successful at eliminating viral infection than was hoped.

SUMMARY OF THE INVENTION

The invention includes methods of treating viral infections. In one embodiment, such a method comprises a treatment protocol including the application of a series of pulses of electrical stimulation to a patient's skin or mucosa, wherein the pulses of electrical stimulation have varying characteristics over the course of the treatment protocol. The pulses may differ in amplitude or frequency. They may alternate between AC pulses and DC pulses.

Apparatus for applying electrical stimulation to treat physiological and pathological conditions such as viral infections is also provided. In one embodiment, the apparatus comprises at least two electrodes and a circuit configured to supply both AC and DC voltage to the electrodes. Other apparatus embodiments include counters for displaying the number of treatments applied. Still other embodiments include replaceable and disposable cartridges comprising electrodes and a battery. The battery may be rechargeable with an external charger. A wide variety of rechargeable/disposable batteries are commercially available with different form factors, costs, etc.

Advantageous electrode designs for the apparatus are also provided. In one embodiment, the electrode comprise an elongated surface for application to the subject's skin or mucosa.

DETAILED DESCRIPTION OF THE PREFERRED EMBODIMENT

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Figure 1:
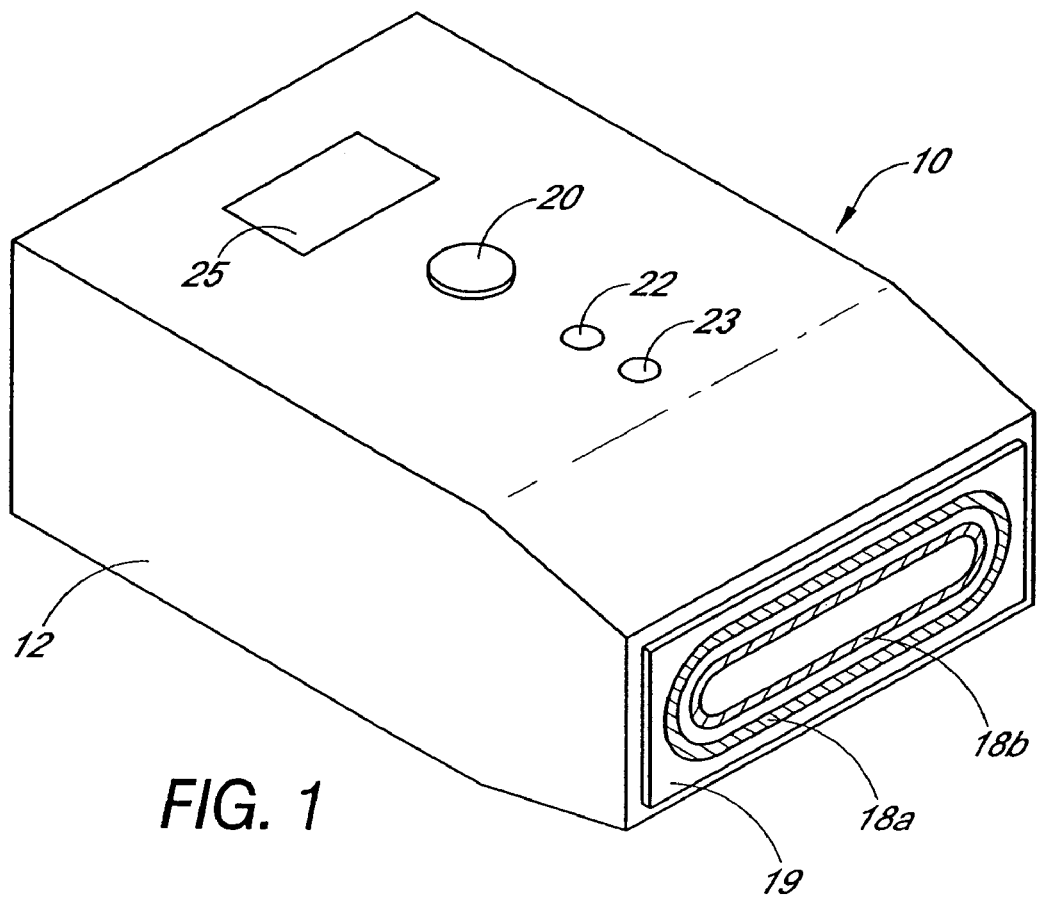
FIG. 1A is a perspective view of one embodiment of an electrical stimulation device.

Referring now to FIG. 1, there is shown one embodiment of the electrical stimulation device of the present invention, useful for treating viral infections. The device 10 includes a housing 12, which is designed to fit comfortably in the hand of the user. At one end, two electrodes 18a and 18b are mounted. The electrodes 18a, 18b, have an elongated surface for application to the user's skin. The elongated electrodes allow for larger electrode to skin surface contact. As shown in FIG. 1, each electrode 18a, 18b may comprise a closed contour. In some embodiments, the electrodes 18a, 18b are concentric closed contours. In the embodiment of FIG. 1, the electrodes comprise circuit traces plated onto a printed circuit board 19 that is attached to one end of the housing 12.

Figure 3:
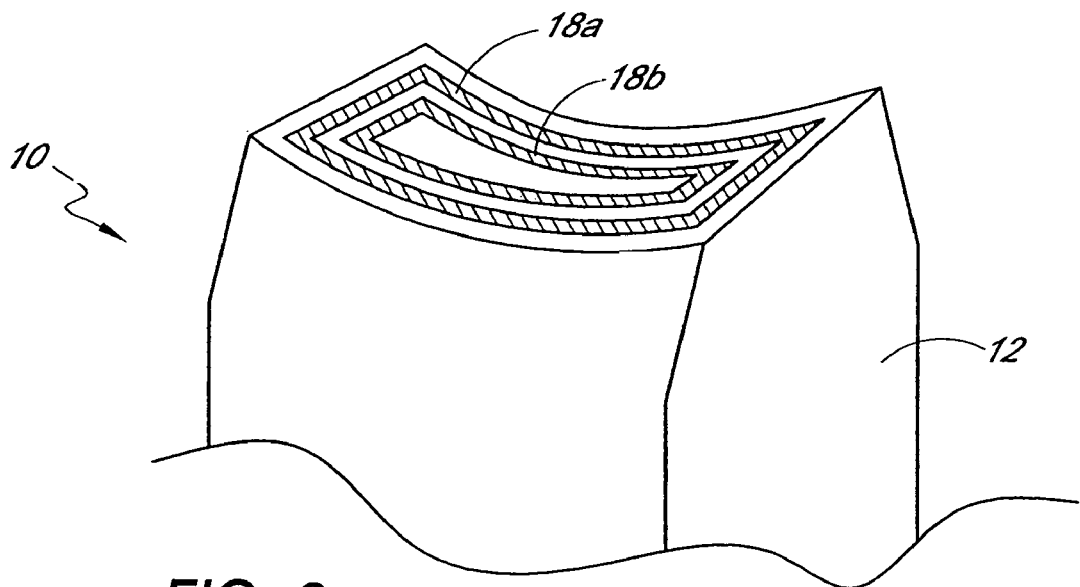
FIG. 3 is a perspective view of another embodiment of an electrical stimulation device.

It will be appreciated that the electrodes may take many forms and shapes. The electrodes 18a and 18b can be oval or elliptical as shown in FIG. 1, rectangular as shown in FIG. 3, or circular, as shown FIG. 4. They may also be square, or any other desired shape, and are preferably gold plated. However, any electrically conductive material can be used. An on/off button or switch 20 that is manually operated is located on the device, which also can include a first LED 22 that is activated when the device is turned on, and a second LED 23 that indicates a low battery condition. An alphanumeric display 25 may also be provided on the device to provide the user with a variety of information concerning device and/or treatment status.

In operation, the electrodes 18a and 18b are placed in contact with the patient's skin or mucosa, and electrical energy is delivered to the electrodes 18a and 18b when the device is turned on. As will be described in additional detail below, the treatment protocol typically involves the application of a series of electrical pulses to the affected area. In this embodiment, the display 25 may show exhibit a count of the number of treatments applied, thus indicating to the user at any given time how much of the treatment protocol has been completed.

Figure 2:
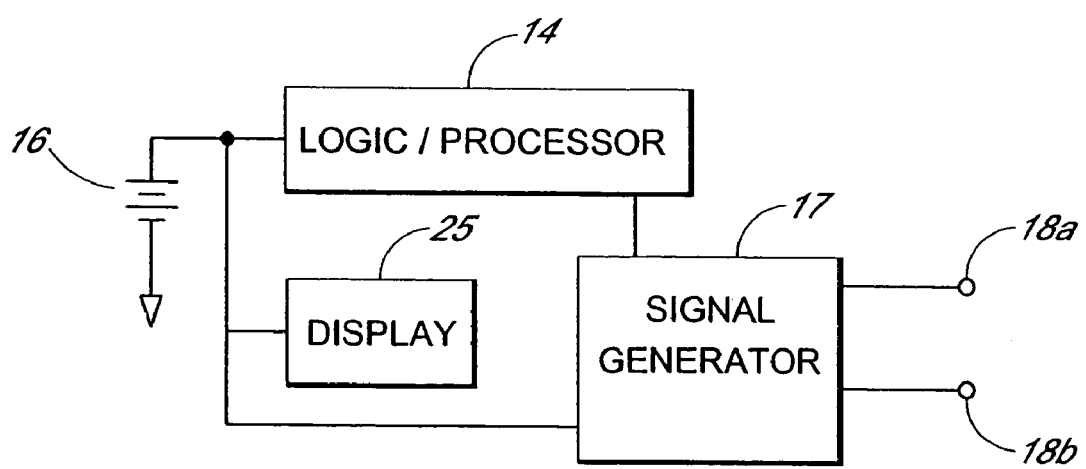
FIG. 2 is a block diagram of an electrical circuit which is provided in some advantageous embodiments of the stimulation devices of the present invention.

FIG. 2 illustrates the circuitry provided inside the housing 12 of some advantageous embodiments of the invention. The device will generally include a battery 16, which may be rechargeable or disposable, coupled to a logic/processor circuit 14, a signal generator circuit 17, and the display 25. The logic/processor circuit 14 drives the display 25 and configures the signal generator circuit 17 to output the desired electrical signal to the electrodes 18a and 18b. Although shown as separate blocks in FIG. 2, it will be appreciated that the logic/processor circuit 14 and the signal generator circuit 17 may be functionally combined, and will typically reside on a common printed circuit board in the housing 12. The types of signals produced by the signal generator circuit 17 in advantageous embodiments of the invention will be described in additional detail below.

The physical size and shape of the device will advantageously vary depending on the specific intended application. The embodiment illustrated in FIG. 1, for example, is advantageously sized for use on the legs and genital area. In this embodiment, the electrical stimulation device 10 is approximately 2-3 inches long, approximately 1-1.5 inches wide, and approximately 0.5-1 inches deep. As noted above, the device 10 is sized so as to fit comfortably in the hand of the user. The circuit traces forming the concentric electrodes 18a, 18b shown in FIG. 1 are approximately 2-3 mm in width, and are plated to a thickness of less than 1 mm. As illustrated in FIG. 3, in an alternative embodiment of the genital applicator, the end of the device 10 which mounts the electrodes is curved so that it is easier to produce contact between the skin of the patient and the entire electrode surface.

Figure 4:
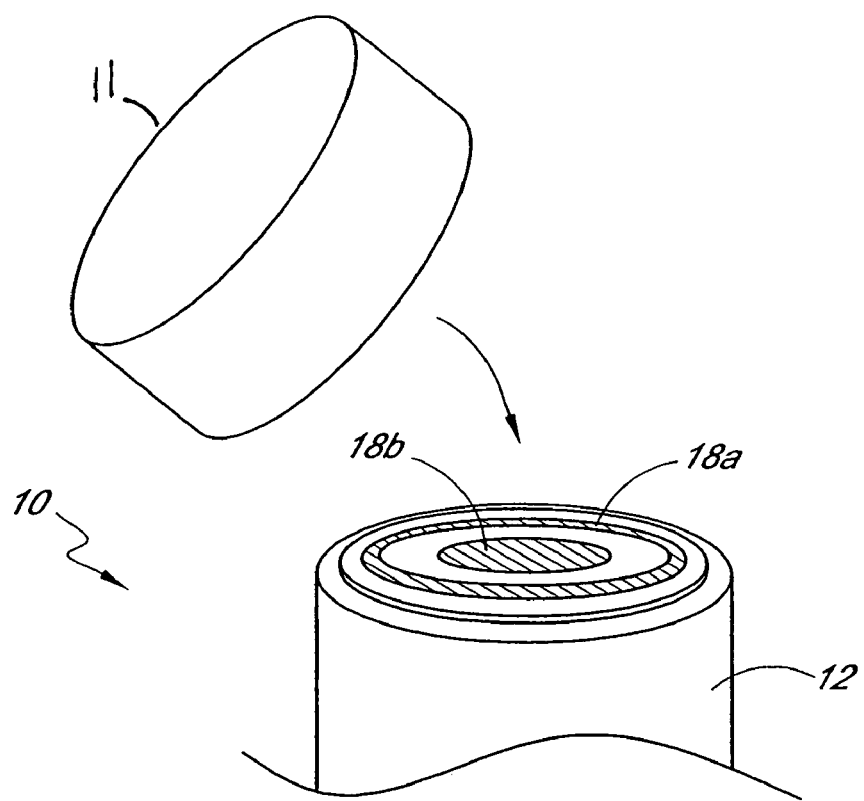
FIG. 4 is a perspective view of another embodiment of an electrical stimulation device.

Turning now to FIG. 4, there is illustrated another embodiment of the electrical stimulation device 10. The device 10 includes a housing 12 and concentric electrodes 18a and 18b at the top end of the device 10. Here, the electrodes 18a and 18b are circular, and the center electrode 18b forms a circular pad rather than a ring. This embodiment is adapted for oral application, and advantageously measures about 0.5 to 0.75 inches in diameter with a length of about 2 inches. This is about the same size and shape of a lipstick or lip balm applicator, and thus is very convenient for carrying in a pocket or purse. In this embodiment, the display 25 may be provided on the bottom flat surface opposite the electrode surface. A cap 11 is also preferably provided for the embodiments of FIGS. 1, 3, and 4. This cap 11 fits over the top end of the device 10 where the electrodes 18a and 18b are located. The cap 11 acts to protect the electrodes 18a and 18b after cleaning with alcohol or hydrogen peroxide and not in use.

Figure 5C:
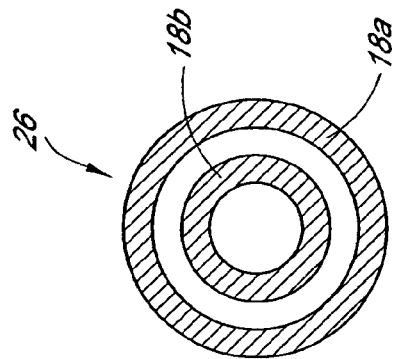
FIG. 5C is an end view of the distal end of the device of FIGS. 5A and 5B, showing the position of the electrodes.
Figure 6C:
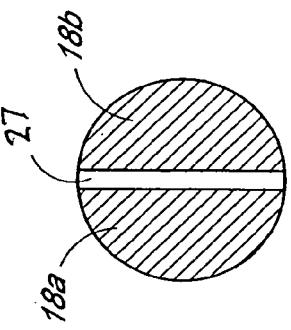
FIG. 6C is an end view of the distal end of the device of FIGS. 6A and 6B, showing the position of the electrodes.
Figure 5B:
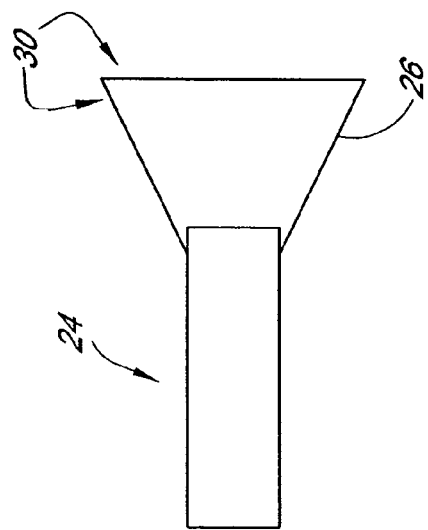
FIGS. 5A and 5B are side views of another embodiment of the electrical stimulation device, showing the disposable activator inserted into, and removed from, the housing.
Figure 6B:
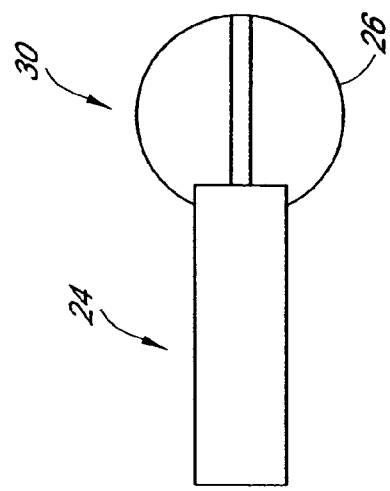
FIGS. 6A and 6B are side views of yet another embodiment of the electrical stimulation device, showing the disposable activator inserted into, and removed from, the housing.
Figure 5A:
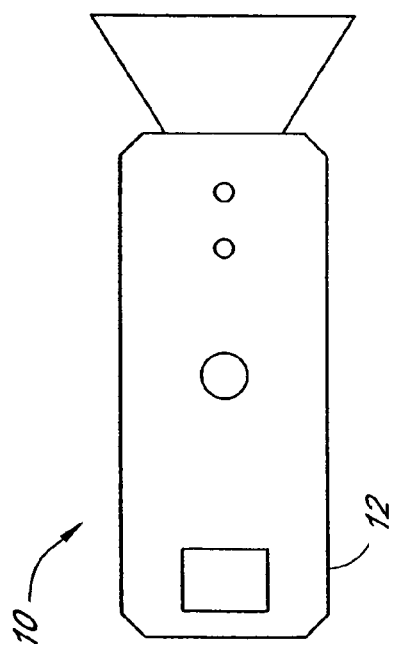
Figure 6A:
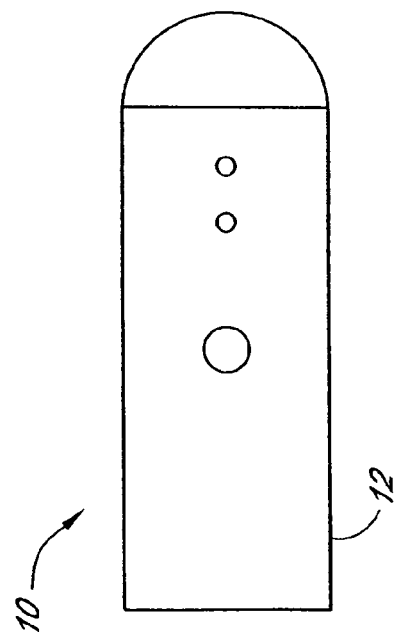

In FIGS. 5A, 5B, 6A and 6B there is shown still other embodiments of the electrical stimulation device 10 of the present invention. In these embodiments, the device 10 includes a disposable electrode cartridge 24 which includes the battery and concentric electrodes 18a and 18b located on the contact head 26 of the device 10, which is located at the distal end 30 of the device 10. The contact head 26 can be flat (FIGS. 5A and 5B) or hemispherical in shape (FIGS. 6A and 6B). The disposable electrode cartridge 24 snaps into the housing 12, but can be easily removed for disposal. As shown in FIG. 5C, the concentric electrodes 18a, 18b, can be circular; alternatively, as shown in FIG. 6C, the electrodes 18a, 18b can be positioned side-by-side, each electrode comprising approximately half of a hemispherical surface, separated by a strip of insulating material 27 along an equatorial line of the hemisphere. This embodiment is advantageous in that the electrodes can be removed and replaced without discarding the entire unit 10.

Figure 7:
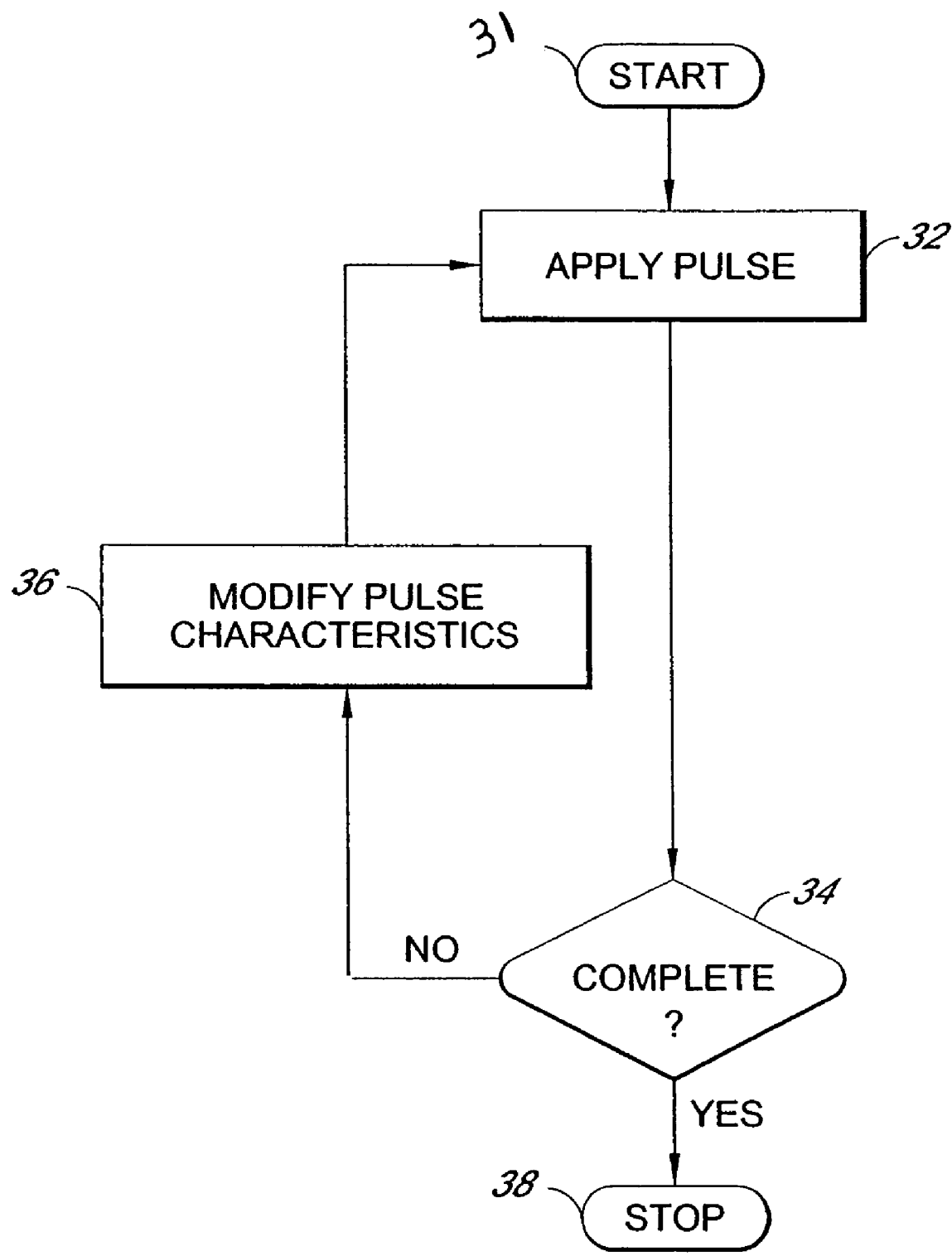
FIG. 7 is a flow chart of an electrical stimulation treatment protocol in accordance with one embodiment of the invention.

The devices described above are used by applying the electrodes to the surface of the affected skin or mucosa and delivering electrical energy to the affected area. It has been found advantageous for a total treatment protocol to comprise a series of electrical pulses, with different pulses being different in signal characteristics. The pulses may differ in one or more of amplitude, frequency, signal type, e.g. AC or DC or any other electrical signal characteristic. It is hypothesized that the different electrical signal characteristics produce different disruptive effects on the virus, thus preventing the survival of those viruses which may already be or which may become resistant to any one form of electrical stimulation This form of treatment protocol is illustrated in FIG. 7, and is initiated at start block 31. At block 32, an electrical signal pulse is applied. At decision block 34, it is determined whether or not the pulse just applied is the last pulse of the treatment. If not, the system moves to block 36, where the device is configured to output a pulse having characteristics different from the previous pulse. Looping back to block 32, the pulse having the new desired characteristics is applied. This process continues until the last pulse of the treatment is applied, and the treatment then ends at stop block 38.

EXAMPLE 3

Human Papilloma Virus

As mentioned above, the pulses may differ in any one or more of a variety of characteristics. The pulses may change in maximum voltage or current amplitude. The pulses may change between AC waveforms and DC waveforms. AC pulses may vary in frequency or waveform such as triangle waves, square waves, or sine waves. As described below, in some advantageous embodiments, the pulses vary in maximum amplitude from approximately 3 volts to approximately 20 volts, and vary in frequency from DC to about 10 kHz.

Two different specific protocols based on the principles described above have been devised. Protocol 1 involves ten 30 second applications of electrical energy, with a one hour break between each one, wherein each 30 second segment is itself divided into sub-segments, which in this embodiment may be 5, 1, and/or 0.2 second intervals. This treatment protocol is defined as follows:

If the ten applications are designated numbers 1 through 10, applications 1, 3, 5, 7, and 9 are as follows:

TABLE 1

5 seconds at 9 VDC
1 second each at 5, 10, 25, 50, and 75 Hz, at 9 VAC peak.
5 seconds at 9 VDC
1 second each at 100, 200, 300, 400, and 500 Hz, at 9 VAC peak.
5 seconds at 9 VDC
1 second each at 500, 300, 100, 50, and 5 Hz, at 9 VAC peak.

Applications 2, 4, 6, 8 and 10 are as follows, all at 9 VAC peak:

TABLE 2

25 step frequency sweep from 5 Hz to 1000 Hz,
0.2 seconds at each frequency, 9 VAC
25 step frequency sweep from 1000 Hz to 5 Hz,
0.2 seconds at each frequency TABLE 2-continued 25 step frequency sweep from 5 Hz to 1000 Hz,
0.2 seconds at each frequency
25 step frequency sweep from 1000 Hz to 5 Hz,
0.2 seconds at each frequency
25 step frequency sweep from 5 Hz to 1000 Hz,
0.2 seconds at each frequency
25 step frequency sweep from 1000 Hz to 5 Hz,
0.2 seconds at each frequency In the above described protocol, the peak voltage remains constant at about 9 V. A more complex protocol, referred to herein as Protocol 2, has also been developed which includes variation in peak voltage as well as variations in waveform and frequency. In this specific protocol, nineteen different pulses that have been found useful and are set forth below in Tables 3 and 4. Twelve of the pulses are AC waveforms, and seven of the pulses are DC waveforms. Table 5 sets forth 10 different pulse sequences which are applied in various combinations to the affected area during a treatment protocol.

Treatment 1
   Sequence 1 at 3V
   hour break
   Sequence 1 at 5V
   hour break
   Sequence 1 at 7V
   hour break
   Sequence 1 at 9V
   hour break
   Sequence 1 at 11V Treatment 2
   Sequence 1 through 10 at 3V
   hour break
   Sequence 1 through 10 at 5V
   hour break
   Sequence 1 through 10 at 7V
   hour break
   Sequence 1 through 10 at 9V
   hour break
   Sequence 1 through 10 at 11V

TABLE 3

|     | 1st second | 2nd second | 3rd second | 4th second | 5th second | 6th second | 7th second | 8th second | 9th second |
|-----|------------|------------|------------|------------|------------|------------|------------|------------|------------|
| A1  | 5 Hz       | 10 Hz      | 25 Hz      | 50 Hz      | 75 Hz      |            |            |            |            |
| A2  | 25 step sweep from 5 Hz to 1 kHz |||||       |            |            |            |
| A3  | 1 kHz      | 2 kHz      | 3 kHz      | 4 kHz      | 5 kHz      |            |            |            |            |
| A4  | 25 step sweep from 1 kHz to 5 Hz |||||       |            |            |            |
| A5  | 5 Hz       | 10 Hz      | 25 Hz      | 50 Hz      | 75 Hz      | 100 Hz     |            |            |            |
| A6  | 1 kHz      | 2 kHz      | 3 kHz      | 4 kHz      | 5 kHz      | 7 kHz      |            |            |            |
| A7  | 5 Hz       | 10 Hz      | 25 Hz      | 50 Hz      | 75 Hz      | 100 Hz     | 125 Hz     |            |            |
| A8  | 1 kHz      | 2 kHz      | 3 kHz      | 4 kHz      | 5 kHz      | 7 kHz      | 9 kHz      |            |            |
| A9  | 25 step sweep from 10 Hz to 2.5 kHz ||||||    |            |            |            |
| A10 | 25 step sweep from 2.5 kHz to 10 Hz ||||||   |            |            |            |
| A11 | 5 Hz       | 10 Hz      | 25 Hz      | 50 Hz      | 75 Hz      | 100 Hz     | 125 Hz     | 150 Hz     | 200 Hz     |
| A12 | 1 kHz      | 2 kHz      | 3 kHz      | 4 kHz      | 5 kHz      | 7 kHz      | 9 kHz      | 10 kHz     |            |

TABLE 4

|    | 1st second | 2nd second | 3rd second | 4th second | 5th second | 6th second | 7th second | 8th second | 9th second | 10th second | 11th second |
|----|------------|------------|------------|------------|------------|------------|------------|------------|------------|-------------|-------------|
| D1 | 3 V | 4 V | 5 V | 7 V | 9 V  |      |      |      |      |      |      |
| D2 | 3 V | 4 V | 5 V | 7 V | 9 V  | 11 V |      |      |      |      |      |
| D3 | 3 V | 4 V | 5 V | 7 V | 9 V  | 11 V | 13 V |      |      |      |      |
| D4 | 3 V | 4 V | 5 V | 7 V | 9 V  | 11 V | 13 V | 15 V |      |      |      |
| D5 | 3 V | 4 V | 5 V | 7 V | 9 V  | 11 V | 13 V | 15 V | 17 V |      |      |
| D6 | 3 V | 4 V | 5 V | 7 V | 9 V  | 11 V | 13 V | 15 V | 17 V | 19 V |      |
| D7 | 3 V | 4 V | 5 V | 7 V | 9 V  | 11 V | 13 V | 15 V | 17 V | 19 V | 20 V |

TABLE 5

| PULSE SEQUENCE | | | | | | | | | | | | |
|----|----|----|----|----|----|----|----|----|----|----|----|----|
| 1  | A1 | D1 | A2 | D1 | A3 | D1 | A4 |    |    |    |    |    |
| 2  | A1 | D1 | A2 | D1 | A3 | D1 | A4 | A1 |    |    |    |    |
| 3  | A1 | D1 | A2 | D1 | A3 | D1 | A4 | D1 | A1 |    |    |    |
| 4  | A1 | D1 | A2 | D1 | A3 | D1 | A4 | D1 | A1 | D1 |    |    |
| 5  | A1 | D2 | A2 | D2 | A3 | D2 | A4 | D2 | A1 | D2 | A2 |    |
| 6  | A1 | D3 | A2 | D3 | A3 | D3 | A4 | D3 | A1 | D3 | A2 | D3 |
| 7  | A1 | D4 | A2 | D4 | A3 | D4 | A4 | D4 | A1 | D4 | A2 | D4 | A3 |
| 8  | A5 | D5 | A9 | D5 | A6 | D5 | A10 | D5 | A5 | D5 | A9 | D5 | A6 | D5 |
| 9  | A7 | D6 | A9 | D6 | A8 | D6 | A10 | D6 | A7 | D6 | A9 | D6 | A8 | D6 | A10 |
| 10 | A11 | D7 | A9 | D7 | A12 | D7 | A10 | D7 | A11 | D7 | A9 | D7 | A12 | D7 | A10 |

Treatment 3
  Sequence 1 through 10 at 3V
  hour break
  Sequence 1 through 10 at 5V
  hour break
  Sequence 1 through 10 at 7V
  hour break
  Sequence 1 through 10 at 9V
  hour break
  Sequence 1 through 10 at 11V
  hour break
  Sequence 1 through 10 at 13V
  hour break
  Sequence 1 through 10 at 15V
  hour break
  Sequence 1 through 10 at 17V
  hour break
  Sequence 1 through 10 at 19V
  hour break
  Sequence 1 through 10 at 20V Treatment 4
  Sequence 1, 3V
  Sequence 2, 5V
  Sequence 3, 7V
  Sequence 4, 9V
  Sequence 5, 11V
  Sequence 6, 13V
  Sequence 7, 15V
  Sequence 8, 17V
  Sequence 9, 19V
  Sequence 10, 20V
  Repeat 10 times with one hour break between each repetition.

In these treatment sequences, the peak AC and DC voltages are specified. Thus, in the case of the application of a DC pulse, the maximum voltage applied will be limited by either the maximum specified in Table 4, or by the maximum specified by the particular treatment segment being applied. Thus, If D7 is being applied at 7 V, the pulse applied is one second at 3V, one second at 4V, one second at 5V, and eight seconds at 7V. However, if D7 is being applied at 20V, the pulse applied is one second each at 3V, 4V, 5V, 7V, 9V, 11V, 13V, 15V, 17V, 19V, and 20V. If D1 is applied at 20 V, the pulse is one second at 3V, one second at 4V, one second at 5V, one second at 7V, and one second at 9V. All AC pulses have peak voltages as specified by the treatment segment being applied.

Treatment should be begun as soon as possible after the onset of symptoms, preferably in the prodromal stage when the characteristic tingling, itching or burning sensation is felt. The distal end of the device is held to the affected skin or mucosa where symptoms are perceived, and treatment is commenced by pressing the "on" button. A designated treatment cycle of about 30 to 60 seconds is automatically initiated. The LED illuminates during this on cycle.

The user generally will not feel any sensation during treatment. By the end of the 10×30 second consecutive treatments of Protocol 1, or by the end of Treatment 1 of Protocol 2, prodromal symptoms should cease. If symptoms continue, or if lesions occur or are still present, it is recommended that treatment be continued. Under protocol 1, this would involve a second course of 10 consecutive 30 second treatments. Under Protocol 2, Treatment 2 as defined above should be administered. If, after this second course of treatments, symptoms or lesions appear or persist, a third course of ten treatments should be carried out under Protocol 1, or Treatment 3 of Protocol 2 should be applied. Finally, if symptoms still remain, Protocol 2 calls for the application of Treatment 4 as defined above.

It will be appreciated that a wide variety of treatment protocols could be devised based on the principles of the invention, and that the two described above are only two specific examples of treatment protocols with the advantageous feature of pulse variability.

A number of device electrode placement protocols can be employed with the present invention and these involve various anatomical sites. Electrode placement sites may be in relationship to neural ganglia where viruses establish residence. For example, the trigeminal ganglion near the ear is a site where HSV-1 (herpes labialis) establishes residence, from which it recurs on the lower lip or face. Therefore this site is ideal for electrode placement and is located in front of the ear (external auditory meatus), below the zygomatic arch, and over the position of the facial nerve and parotid gland. Another neural ganglion example for electrode placement is the sacral ganglion at the base of the spine. This is where HSV-2 (genital herpes) sets up residence from which it recurs in the genital area.

Other electrode placement sites can be in relationship to regional lymph nodes. Examples of these sites would be in the cervical chain of lymph nodes positioned bilaterally at the front of the neck, lymph nodes in the tonsil bed positioned just under the angle of the jaw (junction of horizontal and ascending ramus of mandible), in the axillary chain of lymph nodes positioned under the arms, and in the inguinal lymph nodes positioned bilaterally in the groin.

Further sites for electrode placement can be in relationship to air sinuses such as those in the facial bones of the skull. Examples include the maxillary antrum positioned below the eyes and above the upper teeth, accessed by placement either side of the nose level with the eyes, and the frontal sinus positioned either side of the midline on the forehead just above the eyes.

With the treatment of viral diseases that affect the whole body, and for serious and life threatening viral diseases such as HIV and AIDS, it will be necessary to carry out treatments using placements of the electrical device in other additional anatomical regions using a consecutive pattern of treatments.

In one such protocol, the device is used consecutively on three different anatomical regions of the body. These three sites are referred to collectively as "The Central Location." In this, the first placement site is in the center of the spine, slightly above the level of the shoulders, which is the position of cervical vertebra #7, referred to as C7. The second site is also positioned longitudinally in the center of the spine but between the neck and the base of the spine, which is at about thoracic vertebra #7 (T7). The third and last position is also in the center of the spine but positioned at the base of the lumbar spine equivalent with the 5th lumbar vertebra, referred to as L5.

In another protocol, a further seven anatomical placement sites are employed in addition to the above three sites of The Central Location. Whereas the three previous sites are on the back, or dorsal position, of the body, the seven additional sites are located on the front, or ventral position, of the body. These seven different anatomical regions of the body coincide with the seven "chakras" and channels of energy. Many workers have contemplated that in addition to a network of nerves and sensory organs, there also exists a subtle system of channels and centers of energy (chakras) which affects the physical, intellectual, emotional and spiritual being. These seven regions are used as electrode placement sites and are positioned in seven specific regions of the body ranging from the crown to the sternum, including regions such as the heart. The seven regions are generally referred to as the crown, root, sacral, solar plexus, heart, throat, and third eye chakras. These seven locations physically correspond to the locations of the top of the head, between the anus and the genitals, between the navel and the genitals, between the navel and the base of the sternum, in the center of the chest, centrally at the base of the throat, and above and between the eyebrows respectively.

In these two final protocol examples of treating viral infections of the entire body, the treatment sequences shown in Table 5, and in Treatment 4, are employed whereby ten different pulse sequences are applied in various combinations. Each of the ten separate outputs ramp up consecutively through the various voltage levels resulting in a total treatment time of eight minutes and forty-five seconds in each anatomical site. This regimen may be carried out on each of either the three regions in The Central Location or, additionally, the seven chakra regions as described above, making ten anatomical sites in all.

The three Central Location sites would give a total treatment time of 3×8 minutes and 45 seconds, which is 26 minutes and 15 seconds. The seven chakra regions would give a total treatment time of sixty-one minutes and fifteen seconds. Treatment of all ten locations would give a total treatment time of 87 minutes and thirty seconds. The entire sequence would then be repeated according to the protocol employed which could be, for example, nine repetitions, which is ten treatments in all.

Use of a stimulation device in the treatment of various forms of viral infections are further described in the following specific examples.

EXAMPLE 1

Oral Herpes

A female subject, date of birth Mar. 15, 1975, had a twelve year history of oral herpes infections. Outbreaks tended to occur at the lip borders, especially the lower lip, and were more frequent during cold weather and during times of stress. She reported approximately four to six outbreaks per year, each lasting about 10-12 days. Previous treatments had been unsuccessful.

The subject was given an electrical stimulation device as described above that was configured to apply Protocol 1 as described above. She was instructed to apply the device directly to the infected area or areas, and apply the ten 30 second treatments as described in Protocol 1 above, with a one hour break between each 30 second treatment. The device was configured to automatically step through the ten different electrical pules as shown above as the subject applied the device for the ten consecutive 30 second periods. Thus, the subject only had to place the electrodes on the affected area, press the ON button, and wait for an LED display to turn off after 30 seconds.

After the first treatment, the subject reported that the small veiscles that had begun to develop started to dry up immediately after treatment. The small reddish areas indicating the onset of an outbreak disappeared completely within three days, as did any symptoms of burning or itching.

EXAMPLE 2

Recurrent Genital Herpes

The male subject, date of birth Dec. 25, 1955, had a history of genital herpes for the past 20 years. The outbreaks always occurred on his penis and varied from minor outbreaks to major ones. The subject reported that he had four outbreaks on average each year. He also reported that in his opinion, they often occurred in relation to stress and when he was working very hard physically.

The subject had an outbreak which was preceded by prodrome symptoms. The subject reported that his thighs began to tingle and feel "funny", which is what usually happened just before an outbreak. The day following the prodrome symptoms, the subject noticed a small raised red lump on the top of the head of his penis. The subject started treatment with the device of the present invention on the red spot once every hour for a total of ten treatments using Protocol 1 as described above and as in Example 1. The subject reported that the red spot did not get any larger like it usually did, and was not painful, also a typical since it usually was very painful by the second day. The subject reported that the red spot did not progress to the blister stage. This was the first time in his twenty-year history of having genital herpes that an outbreak did not progress to a blister stage. The subject also reported that there was no release of fluid which was also unusual. The outbreak dried up and disappeared completely after the third day.

The subject had another prodrome stage where the symptoms were similar to those described previously; his thighs started to tingle and burn. The subject noticed that a small outbreak had developed on the underside of his penis and appeared as a raised red spot. This became larger and the subject reported that this had all of the signs of being one of his major outbreaks that he got regularly about once a year. The subject started using the device for treatment as soon as he noticed the outbreak. He used the device every hour as instructed, positioning the tip of the device on the red raised lesion, in the same manner as described above. The lesion did not get any larger once treatment started. The subject reported that after the appearance of the red spot and commencement of treatment, there was no formation of blisters, no wetness or oozing of fluid, and no pain. The subject reported that the outbreak started to resolve itself the day after commencing treatment with the device.

Seven months later, the subject reported that he noticed a little red colored spot appear on the upper side of his penis which swelled and developed into a small bump. The subject reported that there were no signs of a prodrome stage this time. He used the viral device with the same treatment regimen of once an hour, and during treatments, the small bump did not get any larger, and disappeared after a couple of days. The subject reported that this was the "best" outbreak he had in the last twenty years because there was no pain, no swelling, and no discharge, and it was all over in a couple of days.

Three months later, the subject reported that he had a very small outbreak on the left rear thigh. It appeared as a small red spot but there was no evidence of any lesion on his penis. He used the viral device on top of the lesion employing the same protocol as described above, and the small lesion did not get any bigger. The subject reported that there was no blistering, no discharge and no pain. The outbreak cleared up completely in a couple of days.

Five months later, the subject reported the appearance of a small red swelling on the side of his penis. As soon as he saw evidence of the outbreak he started treatment with the device using the once-an-hour protocol described above. The lesion did not progress in size, did not blister, and was not painful. It responded well to the treatment and the lesion disappeared by day three.

EXAMPLE 3

Human Papilloma Virus

A female subject, date of birth Jun. 21, 1951, had a history of lesions appearing on the lower part of her legs, generally on the front aspect between the knee and the ankle. An outbreak usually consisted of 2-3 to six or more lesions, and tended to occur during times of stress. The lesions would become larger over a period of five to seven days, and would dry up and disappear two to three weeks after their appearance. The lesions were diagnosed as being caused by Human Papilloma Virus, for which oral medication and topical cream was prescribed. These treatments were not successful.

The subject then tried the electrical stimulation device of the present invention, using it directly on the lesions for ten 30 second treatments as described above in Examples 1 and 2. She treated each lesion separately, unless two were very close together, in which case the electrodes were placed between the two lesions.

The subject reported that the pain subsided immediately, and that the lesions healed and disappeared within three days.

EXAMPLE 4

Verruca

A male subject, date of birth May 28, 1949, developed a verruca wart on the sole of his right foot. The lesion was positioned at the front and in the center of the planter surface of the foot immediately to the side of the large toe prominence. It interfered with the subject's walking and running. The subject had tried a number of treatments, including 40% salicylic acid pads, but these did not eliminate the wart or the associated pain and discomfort.

The subject used the stimulation device described above for ten 30 second treatments as in Examples 1-3. After the ten treatments, the subject reported that the pain had stopped completely. The lesion was still visible as a raised area on the planter surface of the foot, and a second series of ten treatments was applied, commencing about one hour after the conclusion of the first series of ten treatments. By the end of the second course of treatment, the lesion appeared different in texture, was less swollen, and was not painful. The subject was advised to foot file the region, which he did, after which the affected area looked normal.

Follow up with the subject over nine months following treatment revealed that he was completely pain free, with no evidence that the verruca had returned.

Thus, the method and device described herein were found to be effective in the treatment of viral infection. The treatment with the device not only improved recovery time, but also reduced the frequency of recurrence.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of treating viral infections comprising applying electrical stimulation to the skin or mucosa of a patient, wherein said electrical stimulation is applied as a series of electrical pulses via first and second electrodes located on a surface of an electrical stimulation device, wherein said first and second electrodes are concentric closed contours configured such that said second electrode defines a boundary that surrounds the first electrode and the first electrode surrounds a non-electrode region, and wherein different pulses in said series have different maximum amplitudes.

2. The method of claim 1, wherein said pulses progressively increase or decrease in maximum voltage or current amplitude.

3. The method of claim 1, wherein said pulses progressively increase in maximum voltage or current amplitude.

4. The method of claim 1, wherein said pulses vary in maximum amplitude from approximately 3 volts to approximately 20 volts.

5. The method of claim 1, wherein said first electrode and said second electrode are in a coaxial configuration.

6. A method of treating viral infections comprising applying electrical stimulation to the skin or mucosa of a patient, wherein said electrical stimulation is applied as a series of electrical pulses via first and second electrodes located on a surface of an electrical stimulation device, wherein the second electrode is configured to define a boundary that surrounds the first electrode, and wherein different pulses in said series have different maximum amplitudes, wherein at least one of said series of pulses comprises AC waveforms, and wherein at least one of said series of pulses comprises DC waveforms.

7. The method of claim 6, wherein at least one of said series of pulses alternates between AC and DC pulses.

8. A method of treating viral infections comprising applying electrical stimulation to the skin or mucous membranes of a patient, wherein said electrical stimulation is applied as a series of electrical pulses via first and second electrodes located on a surface of an electrical stimulation device, wherein said first and second electrodes are concentric closed contours configured such that said second electrode defines a boundary that surrounds the first electrode and the first electrode surrounds a non-electrode region, and wherein different pulses in said series have different frequencies.

9. The method of claim 8, wherein said pulses have different maximum amplitudes.

10. The method of claim 8, wherein said first electrode and said second electrode are in a coaxial configuration.

11. A method of treating viral infections with an electrical stimulation device, the method comprising applying alternating periods of AC and DC electrical stimulation pulses to the affected skin or mucosa of a patient.

12. The method of claim 11, wherein said alternating periods of AC and DC electrical stimulation progressively increase in amplitude.

13. The method of claim 11, wherein different periods of AC stimulation have different frequencies.

14. The method of claim 11, wherein said frequencies progressively increase or decrease in frequency within one of said AC periods.

15. A device for treating viral infections comprising:
a housing;
an electrical signal source mounted to said housing, said signal source capable of producing a series of electrical pulses, wherein at least one of said series of pulses comprises AC waveforms and at least one of said series of pulses comprises DC waveforms;
an application surface of said housing for application to a patient's skin or mucous membranes;
first and second electrodes located on the application surface for applying electrical stimulation to the skin or mucosa of a patient, wherein said second electrode is configured to define a boundary that surrounds the first electrode and wherein said electrodes are coupled to said electrical signal source so as to be energized by said electrical signal source; and
a counter mounted to said housing, wherein said counter is configured to display a count of the number of times said electrical signal source has energized said electrodes.

16. The device of claim 15, wherein said counter comprises a multi-segment LCD display.

17. The apparatus of claim 15, wherein said first electrode and said second electrode are in a coaxial configuration.

* * * * *

UNITED STATES PATENT AND TRADEMARK OFFICE
CERTIFICATE OF CORRECTION

PATENT NO. : 7,272,440 B2  Page 1 of 1
APPLICATION NO. : 10/624816
DATED : September 18, 2007
INVENTOR(S) : Leon M. Silverstone It is certified that error appears in the above-identified patent and that said Letters Patent is hereby corrected as shown below:

At column 1, line 7, delete "Ser.No." and insert -- Ser. No. --, therefor. (Consider Space)

At column 2, line 38, delete "*J*" and insert -- *J.*--, therefor.

At column 3, line 37, delete "injures." and insert -- injuries. --, therefor.

At column 8, line 16, after "stimulation" insert -- . --.

At column 8, lines 28-30, below "38." delete "EXAMPLE 3 Human Papilloma Virus".

At column 13, line 46, delete "pules" and insert -- pulses --, therefor.

At column 13, line 52, delete "veiscles" and insert -- vesicles --, therefor.

Signed and Sealed this

Twenty-seventh Day of July, 2010

David J. Kappos
*Director of the United States Patent and Trademark Office*